US006913933B2

(12) United States Patent
Jacobs et al.

(10) Patent No.: US 6,913,933 B2
(45) Date of Patent: Jul. 5, 2005

(54) FLUID DISPENSING ALGORITHM FOR A VARIABLE SPEED PUMP DRIVEN METERING SYSTEM

(75) Inventors: Merrit N. Jacobs, Fairport, NY (US); David D. Hyde, Ontario, NY (US); Christopher M. Parobek, Honeoye Falls, NY (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 380 days.

(21) Appl. No.: 10/005,257

(22) Filed: Dec. 3, 2001

(65) Prior Publication Data

US 2003/0104634 A1 Jun. 5, 2003

(51) Int. Cl.[7] .......................... G01N 1/10; G01N 35/00; G01N 35/08; G01N 21/00; G01N 15/06
(52) U.S. Cl. .......................... 436/180; 436/43; 436/54; 422/50; 422/62; 422/63; 422/67; 422/68.1; 422/100; 73/863.32; 73/864; 73/864.01; 73/864.11
(58) Field of Search .......................... 422/100, 50, 62, 422/67, 63, 68.1; 436/180, 43, 54; 73/863.32, 864, 864.01, 864.11, 864.12, 864.13

(56) References Cited

U.S. PATENT DOCUMENTS

| | | |
|---|---|---|
| 4,005,435 A | 1/1977 | Lundquist et al. |
| 4,008,003 A | 2/1977 | Pinkerton |
| 4,013,396 A | 3/1977 | Tenney |
| 4,223,558 A * | 9/1980 | Schmider et al. ......... 74/421 R |
| 4,344,768 A * | 8/1982 | Parker et al. ................. 436/43 |
| 4,405,294 A | 9/1983 | Albarda |
| 4,575,317 A | 3/1986 | Lindner |
| 4,731,076 A | 3/1988 | Noon et al. |
| 4,845,487 A | 7/1989 | Frantz et al. |
| 4,941,809 A | 7/1990 | Pinkerton |
| 5,020,980 A | 6/1991 | Pinkerton |
| 5,092,037 A | 3/1992 | Pinkerton |
| 5,108,703 A * | 4/1992 | Pfost et al. ................... 422/65 |
| 5,158,441 A | 10/1992 | Aid et al. |
| 5,246,354 A | 9/1993 | Pardinas |
| 5,312,233 A | 5/1994 | Tanny et al. |
| 5,369,566 A | 11/1994 | Pfost et al. |
| 5,482,448 A | 1/1996 | Atwater et al. |
| 5,660,201 A | 8/1997 | Turner |
| 5,761,886 A | 6/1998 | Parkhideh |
| 5,786,012 A | 7/1998 | Peterson |
| 5,863,187 A | 1/1999 | Bensley et al. |

(Continued)

FOREIGN PATENT DOCUMENTS

| | | |
|---|---|---|
| EP | 0 586 280 A1 | 3/1994 |
| EP | 0 512 688 | 9/1996 |
| EP | 0 927 882 | 7/1999 |
| WO | 97/24528 | 7/1997 |
| WO | 99/17917 | 4/1999 |

*Primary Examiner*—Jill Warden
*Assistant Examiner*—Brian R. Gordon
(74) *Attorney, Agent, or Firm*—Wall Marjama & Bilinski LLP

(57) ABSTRACT

A method for improving the fluid dispense rate in a metering system utilizing speed includes the steps of modifying the fluid flow rate profile during a portion thereof so as substantially increase or decrease the speed of the motor during certain portions of a metering cycle in order to improve the efficiency of the metering system. For a variable speed pump producing a sinusoidal speed profile, the pump motor speed can be increased to increase the dispense velocity during the beginning and end of the dispense phase to reduce perfusion and improve metered volume precision or a motor speed profile can be applied which is inverted relative to that of the variable speed pump to produce a constant velocity flow. Alternately or in addition to the above, the home position of the variable speed pump can be shifted to produce fluid velocity during the entirety of a dispense portion of a metering system cycle.

37 Claims, 7 Drawing Sheets

U.S. PATENT DOCUMENTS

| | | |
|---|---|---|
| 6,224,347 B1 | 5/2001 | Clark et al. |
| 6,521,187 B1 * | 2/2003 | Papen ........................ 422/100 |
| 6,551,557 B1 * | 4/2003 | Rose et al. .................. 422/100 |
| 6,589,791 B1 * | 7/2003 | LaBudde et al. ............. 436/55 |
| 6,592,825 B2 * | 7/2003 | Pelc et al. ................... 422/100 |
| RE38,281 E * | 10/2003 | Tisone ........................ 422/100 |
| 6,669,909 B2 * | 12/2003 | Shvets et al. ............... 422/100 |
| 6,689,621 B2 * | 2/2004 | Merten et al. .............. 436/180 |
| 2001/0039053 A1 * | 11/2001 | Liseo et al. ................... 436/43 |
| 2002/0064482 A1 * | 5/2002 | Tisone et al. ............... 422/100 |

* cited by examiner

FLUID DISPENSING ALGORITHM FOR A VARIABLE SPEED PUMP DRIVEN METERING SYSTEM

FIELD OF THE INVENTION

This invention relates to the field of fluid dispensing systems and more particularly to an improved fluid dispensing method for a metering system such as used in clinical analytical apparatus.

BACKGROUND OF THE INVENTION

Automated analyzers, commonly found in clinical laboratories, handle a plurality of samples and are known for identifying analytes in a patient fluid such as blood or sera. Sample fluids are placed into a form which is appropriate to the measurement technique. In typical wet chemistry systems, sample is generally placed in a sample vessel such as a cup or tube in the analyzer so that aliquots can be dispersed to reaction cuvettes or some other type of reaction vessel. A probe or proboscis using appropriate fluidics such as pumps, valves, and liquid transfer lines such as pipes and tubing and driven by pressure or vacuum are often used to meter and transfer a predetermined quantity of sample from the sample vessel to the reaction vessel. In the preparation of an assay, the sample probe or a different probe or proboscis is often required to deliver diluent to the reaction vessel, particularly when a relatively large amount of analyte is expected or found in the sample. A wash solution(s) is also generally needed to clean a nondisposable metering probe. In this instance and as in the preceding, fluidics are needed to accurately meter and deliver wash solutions and diluents.

In addition to sample preparation and delivery, the action taken on the sample that manifests a measurement often requires dispensing of a reagent, substrate, or other substance that combines with the sample to create some noticeable event such as fluorescence or absorbance of light. Several different substances are frequently combined with the sample to attain the detectable event. This is particularly true with immunoassays since they often require multiple reagents and wash steps. For example, in certain assays, a signal reagent is dispensed by a fluidic pump system from a reagent supply onto a bound antibody in a reaction well for detection by a luminometer.

Pumping/metering systems used on clinical analyzers, see FIG. 1, such as those manufactured by the Johnson and Johnson Company, among others, can include at least one variable speed pump which is used to both aspirate a quantity of fluid from a fluid supply, such as signal reagent, and then meter the aspirated fluid into a reaction vessel. Such variable speed pumps are useful in that some do not contain valves or seals and also are constructed from inert materials, which makes their application in the field of clinical chemistry a desired one. Moreover, the mechanical design of the pump affords savings in space and manufacturability, which is not found in other conventional servo or other constant speed pump types.

An exemplary variable speed pump used in the above pumping/metering system of a clinical analyzer utilizes mechanical means such as an eccentric cam, which is coupled to the pump piston. This form of interconnection in turn drives the piston both rotationally and reciprocally as shown in FIG. 4. A result of this operation is that the resulting fluid flow rate is variable throughout a metering cycle, this profile being consistent with the number of revolutions per minute of the motor driving the pump. For the pump shown in FIGS. 4(a)–4(d), the fluid flow rate profile for both the aspirate and the dispense phase of a fluid metering cycle is sinusoidal in nature ranging between zero at the onset and the conclusion of each phase and a maximum value there between as shown in FIG. 5.

As noted, there are certain advantages afforded by the above-noted pump designs. In the preceding pump design, for example, a single mechanism permits both rotational and translational movement of the piston. Therefore, utilization of these and other variable speed pump types is desirable for a number of varied types of metering systems covering numerous applications that involve liquid dispense. However, there are also some associated problems, depending on the end application, that can result with their implementation.

First and as previously noted, mechanical design of the above-described variable speed pump causes the fluid flow rate at the beginning of the dispense phase to rise gradually from zero and towards the end of the dispense phase to gradually drops to zero, as shown in the profile of FIG. 5. It has been determined that an insufficiently low velocity eliminates the fluid shear effect for fluid leaving a dispense tip or nozzle and therefore results in a substantial amount of fluid remaining either on the exterior of the probe, as a result of perfusion, if at the beginning of the dispense phase or within the metering probe, if at the end of the dispense phase. The amount of residual fluid can be variable which can be problematic. In particular, the metered volume variability is of particular concern when small volumes of fluid (e.g., less than 100 $\mu$l) are being metered, such as into a reaction vessel or well in the case of a clinical analyzer, and moreover when the fluid being metered is volatile. Residual fluid which is left on the end of the dispense tip can also evaporate various amounts when the duty cycle of the metering system is variable. For example and assuming this variation is as much as 2–3 $\mu$l, then evaporation of the residual fluid will result in about a 3 percent change at 100 $\mu$l of metered fluid volume and about a corresponding 30 percent change at 10 $\mu$l.

There are several other consequences/problems relating to the evaporation of residual fluid left at the tip of the metering probe, aside from errors in metered fluid volume. Residual fluid left on the end of the tip is exposed to atmosphere. Therefore and depending on the nature of the fluid, oxidation may result which could change the chemical nature of the fluid, thereby causing an impact upon the measurements taken, for example, by the clinical analyzer using the pump/metering system described herein, which can degrade performance. This latter impact can be more significant in nature than errors that are created in measured metered fluid volume.

In addition to the above consequences, dried residual fluid can also clog the orifice of the dispense nozzle and thus impact the flow of fluid therefrom. This issue is of particular concern when the orifice size is very small or when the flow direction and speed are critical parameters.

Yet another issue relating to residual fluid being left on the outside of the metering probe through perfusion is when the nozzle (e.g., metering probe) needs to be moved abruptly. The action of any abrupt movement can cause fluid to be dislodged from the exterior of the metering probe. Consequences from this undesired event range from cosmetic issues, given that periodic maintenance of the signal reagent module may be required, to a profound impact upon metering volume. The latter impact can be especially felt if the above described movement of the probe does not occur on each and every metering cycle.

Yet still another especially severe consequence, depending on the application, is cross contamination of fluids, which can have extremely disastrous results depending on the chemicals that are being metered.

SUMMARY OF THE INVENTION

It is a primary object of the present invention to alleviate the above-described problems found in the prior art.

It is another primary object of the present invention to efficiently improve the dispensability of at least one fluid in a metering system utilizing a variable speed pump.

It is yet another primary object of the present invention to significantly reduce the risks associated with perfusion and residual volume in a metering system.

It is yet another primary object of the present invention to improve the performance characteristics of metering systems in clinical analyzers and other apparatus.

It is another primary object of the present invention to reduce the errors associated with metering volume to a reaction vessel, particularly with small or micro volumes.

Therefore and according to a preferred aspect of the invention, there is described a method for improving the dispensability of a metering system, said metering system including at least one dispense nozzle, a fluid supply, and at least one pump fluidly interconnecting said at least one dispense nozzle and said fluid supply, said pump including a pump and having a mechanism which produces a variable fluid flow rate profile for a constant motor speed, said method including the steps of:

aspirating fluid from said fluid supply;

dispensing aspirated fluid through said at least one dispense nozzle; and modifying said variable fluid rate flow profile using said pump motor during at least one of said aspirating and dispensing steps so as to effect the relative velocity of dispensed fluid.

According to one version and depending on the profile, the speed of the pump motor can be varied along any portion of the fluid flow rate profile in order to effect the fluid flow rate and hence the fluid velocity exiting the dispense nozzle. For example, for a sinusoidal flow profile having a zero fluid flow rate at the beginning and the end of the dispense phase, the speed of the motor can be increased during these portions to increase the rate of fluid being dispensed at the dispense nozzle. According to one version, the speed of the motor can also be increased during the aspirate phase in order to permit a more gradual buildup for the overall transition and thereby permit use of pump having a lower motor torque requirement.

According to another version, a reference or home position of the motor can be shifted in order, for example, to shift at least a portion of the profile and produce, for example, given the above profile, an increase in relative fluid velocity/flow rate at the end of a dispensing step.

According to another preferred aspect of the invention, there is described a method for improving the dispensability of a metering system used in a clinical analyzer, said metering system including at least one metering tip, a fluid supply, and at least one pump fluidly interconnecting said at least one metering tip and said fluid supply, said pump including a pump and having a mechanism which produces a variable fluid flow rate profile for a constant motor speed, said method including the steps of:

aspirating fluid from said fluid supply;

dispensing aspirated fluid through said at least one dispense nozzle into a reaction vessel; and modifying said variable fluid rate flow profile using said pump motor during at least one of said aspirating and dispensing steps so as to effect the relative velocity of dispensed fluid.

According to yet another preferred aspect of the invention, there is described a metering system comprising at least one dispense nozzle; a fluid supply; and at least one pump fluidly interconnecting said at least one dispense nozzle and said fluid supply, said pump including a motor and mechanical means for producing a variable fluid flow rate profile for a constant motor speed during at least one phase of a metering cycle including an aspiration phase and a dispensing phase, said system further including means for modifying the fluid rate profile of said pump during at least one phase of said metering cycle so as to effect the relative velocity of dispensed fluid.

A realized advantage of the above method and apparatus is that by increasing the fluid flow rate at the beginning of the dispense phase, perfusion is substantially reduced at the dispense tip, thereby reducing metering volume errors in a clinical analyzer, particularly at smaller fluid volumes and also preventing the risk of cross contamination, oxidation, and evaporation.

Another significant advantage achieved by the present invention is a faster dispense rate at the start of the dispense phase of the metering event which significantly reduces perfusions while doing this in a manner that does not increase the maximum fluid velocity. The advantage of doing this without increasing the maximum dispense rate is important since is reduces any tendency for splashing.

Another advantage of the present invention is minimizing or virtually eliminating the presence of residual fluid on a metering nozzle at the end of a dispense phase which helps keep the probe clean and free from clogging, improves metered volume precision and reduces the evaporative effects on the fluid remaining in the probe since this fluid is not directly exposed to air or light, especially those fluids which are sensitive thereto. Furthermore, and by increasing the fluid velocity at the very end of the dispense phase permits formation of an air bubble or pocket at the end of the metering probe, further reducing the risk of evaporation.

These and other objects, features and advantages will become readily apparent from the following Detailed Description, which should be read in conjunction with the accompanying drawings.

DETAILED DESCRIPTION

The following description relates to certain preferred embodiments of the present invention as used in a specific fluid dispensing system (e.g., a signal reagent subsystem) pertaining to a specific clinical analyzer manufactured by Johnson and Johnson. It should be readily apparent from the description which follows, however, that the inventive concepts of the present metering method can be used with other fluid dispensing systems which either utilize or could utilize at least one variable speed pump such as in various pharmaceutical, manufacturing, chemical, diagnostic, or scientific applications involving liquid dispensing into a container, or onto a substrate, such as a semiconductor chip. In addition, certain terms are used throughout the course of discussion such as "top", "bottom", "above", "below", "above", and "beneath" among others. These terms are intended only to be used as a frame of reference for the accompanying drawings and are not intended to be limiting of the inventive concepts described herein.

Figure 1:
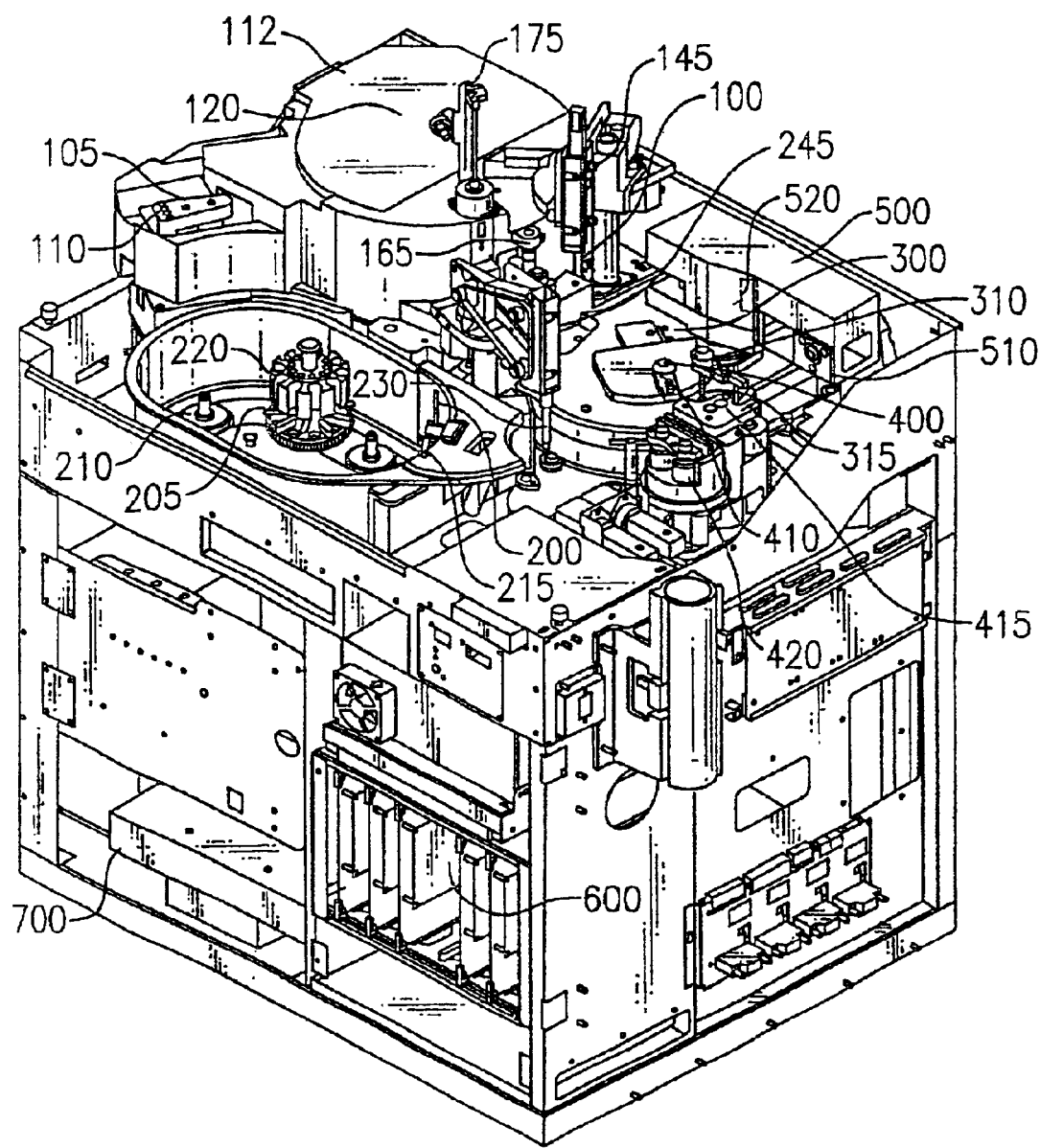
FIG. 1 is a top perspective view of a clinical analyzer.

Referring to FIG. 1, a clinical analyzer for use in the herein described embodiments is shown. The analyzer is designed to conduct automated enzyme immunoassays (EIAs) for analytes including hormones, vitamins and related compounds, infectious disease markers, cancer markers, therapeutic drug monitoring, abused drug analysis, and other analytes amenable to analysis by EIA. The following discussion is to provide background of the overall operation of the analyzer as a prelude to a description of the present invention.

A reagent management system conducts reagent scanning for input into a data processing mechanism for the analyzer and meters and dispenses reagent to a plurality of reaction wells via a reagent probe 100. Reagent packs 105 are external to the system but are manipulated by the reagent management system; these packs are configured to contain the reagents necessary to conduct an immunoassay. Typically, these reagent packs 105 contain one or more antigenic or antisera components used to combine with the analyte and provide adhesion to or with a reaction well. Preferably, reagent packs 105 are configured with a spring-loaded supply of reaction wells of an appropriate volume and geometry for the assay. Preferably, 0.35 ml conical wells 135 coated with a material complimentary to the reagents are used as reaction wells, see FIG. 2. Well coatings can comprise materials such as streptavidin and/or other materials useful for immunochemical analysis, as is well known in the field, to facilitate binding by a biotinylated antigen or antibody to which an analyte binds as part of the assay chemistry.

The reagent management system of the analyzer includes a number of subsystems and components, herein referred to briefly. Additional details can be found in commonly assigned and copending U.S. Ser. No. 09/482,599, entitled: Failure Detection in Automated Clinical Analyzers, the entirety of which is herein incorporated by reference.

An autoload station 110 shuttles reagent packs to a reagent supply subsystem 112 by any suitable drive mechanism. Preferably, a system of epicyclic gears is used in which a geared ring is fitted with a slotted overlay corresponding to the shape of the reagent pack. The reagent pack is then inserted into a slot along the movable portion of the subsystem 112 and is driven in a circular motion by a pinion on the interior of the ring. In this way, the reagent packs 105 can be stored for access and rotated to an appropriate position for aspiration and dispensing by the reagent management system. A reagent supply cooler 120 cools the interior of the reagent supply subsystem 112 according to the functional requirements of the specific reagents (typically about 3–15° C., preferably about 4–10° C.).

Figure 2:
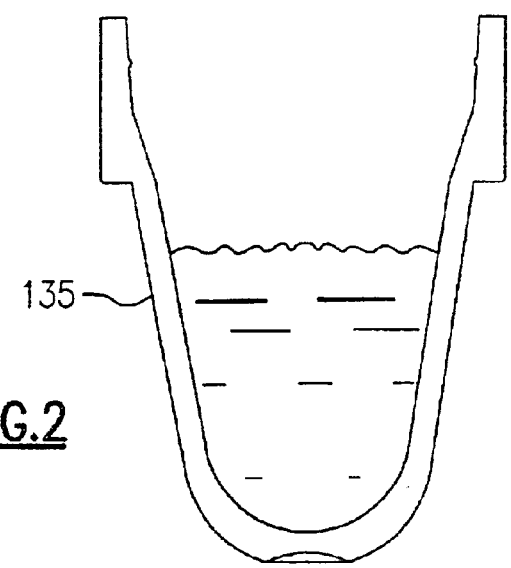
FIG. 2 is an elevational view of a reaction well used in the clinical analyzer of FIG. 1.

In this way, the reagent supply cooler 120 maintains the reagents and reaction wells 135, FIG. 2, at the appropriate humidity and temperature. A reaction well shuttle 125 extracts the reaction wells and deposits them into an outer ring of an incubator used in the processing system. The wells are extracted from their storage areas (preferably, the reagent packs 105) by an extraction device (not shown) comprising a portion of a well dispenser 175 that functions in concert with the reagent well shuttle 125. This dispenser can comprise any convenient mechanism such as a hydraulic plunger having a prong at one end corresponding substantially to the shape of the reaction well. This mechanism is preferably pivotable so that once grabbed, a reaction well can be moved to a portion of the instrument wherein it can be filled with reagent and/or sample.

The reagent metering subsystem 112 is comprised of a pivotable reagent metering arm 145 having a reagent probe 100 movably attached thereto. The arm 145 is pivotable such that it can position the reagent probe 100 to dispense reagent and/or diluent into the reaction well. The arm is also configured to permit vertical motion so as to lower itself into the vicinity of the reaction well using any conventionally known drive mechanism. Preferably, a stepper motor with fine steps connected to a rack and pinion drive is utilized to permit at least about 390 steps per cm of vertical motion. Where pivoting is desired, a stepper motor with fine steps is also preferred (generally, at least about 1720 steps per revolution of the shaft used to rotate the probe or probe arm are desired) with the pinion comprising or attached to the outer diameter of the shaft that is rotated. Control of stepper motors, and hence probe and mechanism movement, is accomplished through techniques which are well known in the art such as those described in U.S. Pat. No. 5,646,049, which is entirely incorporated herein by reference.

In operation, the reagent probe 100 aspirates and dispense fluids via connection to a fluidic system(s) comprised of valves, pumps, tubing and the like. It is preferably charged by vacuum and can disperse by release of vacuum or by pressurization. Whenever reagent metering involves aspirating and dispensing different reagents, it is desirable to include a wash step so that the reagent metering probe 100 does not carry over reagent from one step of an assay into a different step of the assay or into a different assay. This helps avoid small inaccuracies. The wash step involves flushing the probe 100 with a wash fluid after delivery of each reagent component. Thus, the reagent probe 100 is also connected via fluidics systems to a wash station 165. The probe 100 can be charged and dispense wash fluid by vacuum or by pressure. The reagent probe wash station 165 provides an enclosed space for the metering probe 100 to conduct the wash step. In operation, the metering probe is lowered into a wash cylinder 175 of the wash station 165, wash fluid is charged through the probe and into the wash cylinder 175 and evacuated through the outlet port, 160. Wash fluid is also charged through an inlet port 170 to wash the exterior of the reagent probe 100.

A sample manipulation system loads and meters sample into the appropriate reaction wells. This system is also capable of providing input to the data processing system 600 via a bar code reader 200 that reads bar codes that may be placed on patient sample vessels such as test tubes and the like. The sample manipulation system is also comprised of a number of subsystems and components. The sample supply subsystem is one which is comprised of a bar code reader 200 for inputting sample identification data as described above and a sample tray conveyor 205, one or more sample tray transports 210, and positioner 215 for moving sample to the sample metering station adjacent to the sample positioner (i.e. the position into which proboscis 230 is lowered, as described below).

The sample tray conveyor 205 can be any conveyor system for moving vessels and can employ an electrically or mechanically movable magnetic drive that propels a carousel 220 atop a sample tray transport 210 having a magnetic or ferrous component attractive to the magnetic drive. The preferred sample tray conveyor is an elliptical magnetically driven tracked system. In this system, the sample tray is preferably a carousel 220 that sits atop a transport 210 that has a piece susceptible to magnetic attraction. This enables it to be moved around the ellipse through the rotation of a magnetic field around the perimeter of the elliptical track from a position beneath the sample trays. In this configuration, the outer diameter of the sample tray can be geared so that the tray can be rotated about its own central axis by a geared piece such as positioner 215 adjacent to the bar code reader 200 (or at any other convenient location around the exterior of the elliptical track).

A sample metering subsystem aspirates samples and dispenses them into reaction vessels via a proboscis 230. The proboscis and its related metering arm 245 are preferably similar in design to the reagent metering arm 145 described above. Disposable tips (not shown) through which sample can be aspirated and dispensed are preferably fitted on the proboscis 230 and are disposed after each aspiration and delivery of sample. The tips are preferably conical with the apex of the cone pointed toward down. Appropriate robotic commands are used to position the proboscis over the tips and then temporarily attach the tips via force (injection of the proboscis into the hollow portion of the tip). For convenience, a supply of tips can be maintained on a tip supply carousel (not shown). The tips can likewise be removed by raising the proboscis drive to its top most travel, activating an ejector sleeve (not shown). Generally, disposable tips are comprised of a molded thermoplastic such as polyethylene or polypropylene. Such tips avoid direct and repeated contact of sample and a singular proboscis end.

In operation, the sample metering subsystem functions similarly to that of the reagent metering subsystem. Sample, loaded on sample carousel 220, is driven to a location reachable by the proboscis 230. After having loaded a disposable tip onto the proboscis, the system pivots the proboscis directly overhead a sample vessel. The proboscis 230 is then lowered into a vessel, such as a tube on the carousel 220, where it aspirates a quantity of sample sufficient for the assay to be conducted. The proboscis 230 is then pivoted to a position that is overhead a reaction well residing in an outer ring (not shown) where the sample is dispensed. It is preferable that sample is dispensed into the well before reagent has been dispensed into the well. The proboscis 230 can then be used to validate the proper metering of the sample into the well. This is accomplished by fitting the proboscis with a sensor, such as an optical sensor (not shown) on the sample metering arm 245. The sensor is in communication with a transducer (not shown) and the data processing system 600 and preferably detects the level of the sample by pressure differential, through capacitance, or reflected energy as is known in the art. An optical sensor can also be used to guide the proboscis to its proper or "home" position. After metering and measuring the sample, reagent is preferably dispensed into the well as described above. Mixing of sample and reagent is accomplished by dispensing reagent into the well containing sample with sufficient velocity to give partial mixing. Further mixing is accomplished by moving the concentric interior rings (not shown) of the incubator at rapidly changing velocities.

Some assays require dilution of the sample. In this instance, sample is first metered into a dilution vessel (not shown) that is preferably substantially similar to the reaction wells previously described except that they are not generally treated with any reagent or other materials to which added reagent would adhere. That is, the dilution vessels are functionally inert within the context of the immunochemical reactions of interest. Proboscis 230 is used to meter the sample as in other assays. Dilution wells are placed in the outer ring (not shown) of the incubator during the dilution operation. The reagent probe 100 meters and dispensed diluent into the dilution well. Preferably, diluent is added to the dilution well after the addition of sample but it is possible to add it before or after any component. It is also possible though less desirable to configure assays so that reagent is added before addition of sample or before addition of diluent. After diluent is added, the diluent and sample are mixed by aspiration of reagent and sample in the proboscis 230 and dispensing the combined fluid back into the well 135. This process of mixing by aspiration and dispensing is referred to as "swish mixing". Upon completion of mixing, the proboscis 230 aspirates the diluted sample and dispenses it to a reaction vessel (well) on the outer ring of the incubator for completion of the assay.

In the processing system, reaction wells containing sample, reagent, and (optionally) diluent are mixed with signal reagent and are incubated. Chemilluminscence or other appropriate signal generation of the reaction of sample analyte and reagent(s) is also read in this system. Well wash arm 310 and well wash probe 315 are the principal components of a well wash subsystem whose function is to wash the reaction wells and remove sample and unbound reagent (analyte is bound to the walls of the reaction vessel, along with reagents that manifest the signal that is read later).

The rings of the incubator 300 are preferably of independent concentric epicentrically geared rings similar to that described for the autoload station 110. Such a configuration can be driven by pinions (not shown) or other convenient means. Recesses are conveniently placed along the curvature of the ring into which reaction and dilution wells can be placed. The temperature and humidity are controlled within incubator 300 for a time and at a temperature appropriate to the assays being performed. Incubation time can differ from assay to assay and is under the control of the data processing system 600.

Returning to the well wash subsystem, after appropriate incubation, well wash probe 315 (which is preferably similar in design to the reagent probe 100) is manipulated so that is aspirates and dispenses sample and unbound reagent out of the reaction wells 135, FIG. 2, and then dispenses wash fluid into the wells, aspirates and dispenses again. Thus, to this point within the reaction wells, reagent and analyte have reacted and have been adhered to the well. The well wash arm 310 has removed materials that have not reacted and/or could otherwise interfere with sample reading.

It is also possible to configure such an instrument so that the unmeasured materials would adhere to a reaction vessel and the contents of the vessel would be further processed or be subject to some reading. In such a case they would then have to be aspirated and dispensed to another vessel (not shown).

Upon completion of well washing, the well wash arm 310 articulates movably attached well wash probe 315 to a position to aspirate sample and unbound reagent and dispense wash fluid to a reaction well 135, FIG. 2. Generally, wash fluid is dispensed as the well wash probe 315 is lifted out of the reaction well. A signal reagent subsystem comprises a signal reagent arm 410, a signal reagent probe 400, signal reagent (packs) 420, and a prime/pump assembly 415 as its major components. Signal reagent probe 400 (which is preferably similar in design to the other probes already described), movably attached to signal reagent arm 410 aspirates, transports, and dispenses signal reagent from signal reagent pack 420 to the reaction wells in the incubator. Signal reagent arm 410 is fitted to the prime/pump assembly 415 for this purpose. Additional detail relating to the signal reagent subsystem is provided in a later portion of this discussion.

Signal reagent is a composition that contains at least one component that produces a signal upon combination with the reacted reagent/sample combination (e.g., luminol derivatives). Luminometer 500 is comprised of a fiber optic bundle 510 that communicates with photomultiplier 520 which is in further communication with data processing system 600. In operation, the fiber optic bundle 510 is positioned over the sample with mixed reagent and, optionally, diluent. Chemilluminescent signals generated by the reacting reagent/sample combination are then transmitted to the photomultiplier that converts the light signal to an electrical signal for processing according to conventional digital techniques. An internal reference (not shown) can be used for calibration of the luminometer 500.

The data processing system 600 of the herein described analyzer is an integrated array of circuitry used to coordinate the function of the systems and subsystems, conduct system diagnostics, calibrate instrumentation, record results, and analyze results. It includes well known processing devices such as microprocessors and may be in electronic communication with any number of external processing systems. For example, it may be linked through a local area network to other analytical instrumentation so that test are scheduled and results are compiled and reported for a number of different assays, some of which are not conducted on the instrument described here.

A number of other systems are ancillary to the primary functioning of the herein described analyzer. These include, a supply center 700 for storage and dispensing of wash fluids. These fluids can be stored in a large container maintained under pressure by a pump. Appropriate fluidics such as tubes, pumps, and valves are used to drive the fluid to a working bottle that can be used to mix the fluid with other fluids prior to injection to one of the systems such as the reagent management system. Here too, the fluids can be driven via appropriate fluidics using pumps generating a positive force or vacuum. A filter such as a micropore filter is generally placed in one or more of the fluidics line prior to a point in which a fluid will be dispensed so that it is degassed enroute to the appropriate dispenser. This occurs as a result of the pressure gradient across the filter and leads to improve accuracy and precision in metering the fluid.

To summarize then, an assay is generally conducted as follows. Reagent packs 105 containing reagents specific to the assays to be performed are loaded into auto-load station 110. The reagent packs are then shuttled into reagent supply substation 112 within the reagent supply carousel. Sample tubes are loaded onto sample carousel 220 which is placed in the sample conveyor. The sample conveyor 205 which moves the sample carousel to the positioner 215 which rotates the sample tray so that barcode reader 200 can input data about the identity of each sample tube into the data processing system 600 for assignment of tests and in preparation of result reports. Sample metering arm 245 moves proboscis 230 to a location above sample tubes. Proboscis 230 (with attached tips) is then lowered into the tube and aspirates a predetermined quantity (e.g., 10, 10–80 $\mu$l) of sample. A reagent pack 105 corresponding to an assay to be performed on the aspirated sample is then moved beneath the well dispenser 175 where a well is pushed into well shuttle 125 and then into the outer ring within incubator 300. This outer ring is then rotated to a position beneath proboscis 230. The sample metering probe or proboscis 230 is then rotated to an appropriate position above the well and dispenses a predetermined quantity (e.g., between about 10–80 $\mu$l) of sample into the well corresponding to the assay to be performed.

Reagent metering probe 100, which has been moved into an appropriate position by reagent metering arm 145, is in a position atop the reagent pack. Between about 20 and 160 $\mu$l of reagent(s) are then aspirated. The outer ring of the incubator is then rotated to a position beneath reagent metering probe 100. The reagent metering probe 100 is then rotated to an appropriate position above the well and dispenses aspirated reagent into the well corresponding to the assay to be performed. The well is then rotated in the outer ring of the incubator 300 for a time that is dependent on the assay to be conducted and is then moved to a position on the inner ring of the incubator by shuttle 260. The well wash probe 310 dispenses wash solution, aspirates unbound reagent and wash solutions, and evacuates the solution via system fluidics. The inner ring of the incubator is rotated so that the washed well is in a position in which signal reagent can be dispensed into the well via signal reagent probe 400. Signal reagent arm 410 moves the signal reagent probe 400 in position above signal reagent, which is then aspirated. The probe is then moved to a position atop the well where it is dispensed. The well is then incubated for 5 minutes and rotated to a position where it is accessible to the luminometer 500 which reads one or more chemilluminescent emissions, converts the signal to an electrical one via the photomultiplier 520 and, passes the readings to the data processing system 600. The data processing system 600 then uses the signal to attain and communicate a clinical result. The reaction well 135, FIG. 2, is then disposed of by conventional means.

Figure 3:
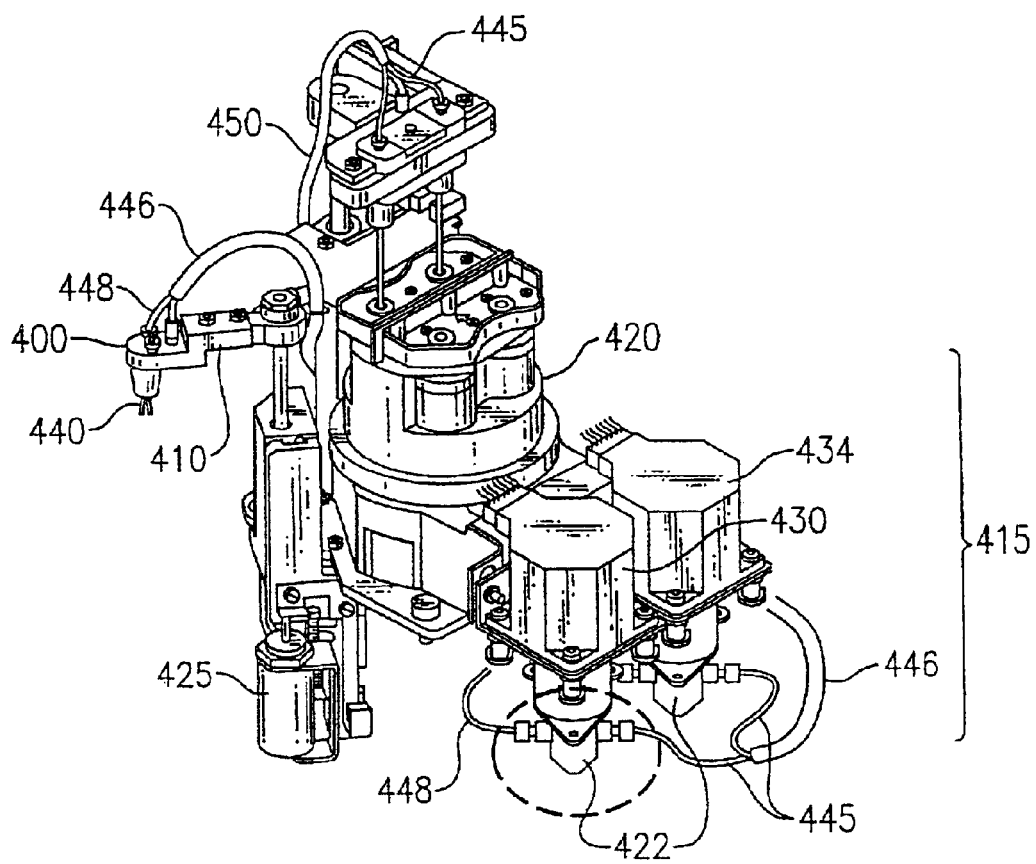
FIG. 3 is a top perspective view of a signal reagent subsystem of the analyzer of FIG. 1.
Figure 4A:
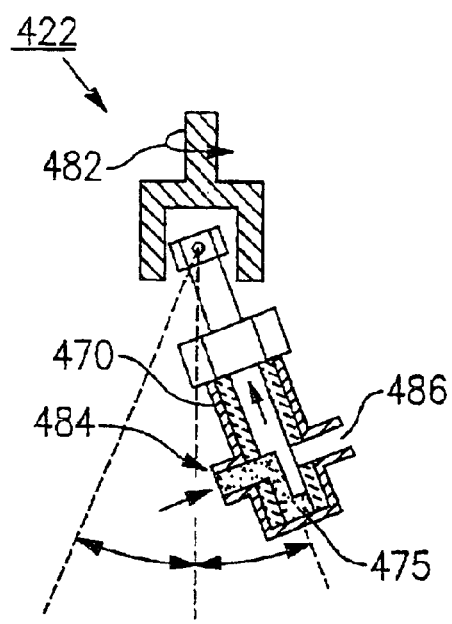
FIGS. 4(a)–4(d) are partial sectional views of a pump used in the signal reagent subsystem of FIG. 3.
Figure 4B:
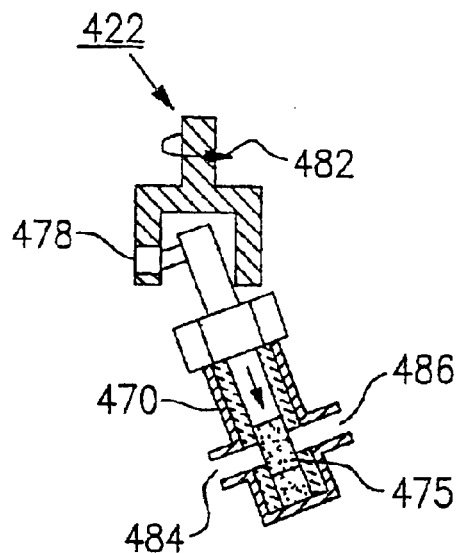
Figure 4C:
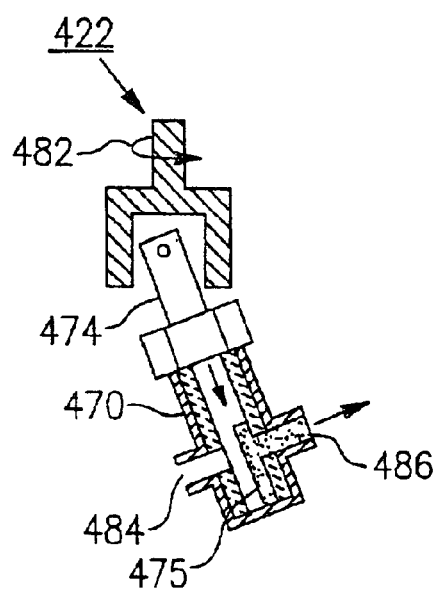
Figure 4D:
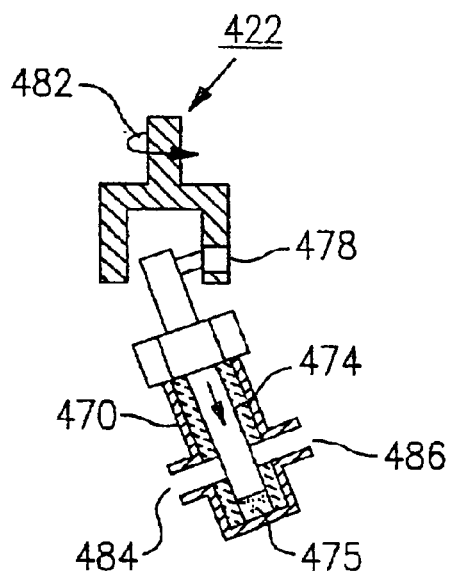

Referring to FIG. 3, the signal reagent subsystem is herein further described for purposes of the present invention. As noted above, the subsystem includes a reagent supply consisting of a pair of reagent packs 420, each of which are supported upon a carousel 422. A quantity of reagent fluid is metered through a metering probe 400 having a pair of dispense tips 440 extending downwardly from the signal reagent arm 410, the arm being both pivotally and vertically movable through a pair of stepper motors, only one of which 425 is shown in the FIG. in order to bring the reagent probe in proximity with a reaction well 135, FIG. 2. The prime/pump assembly 415 includes a pair of corresponding pumps 430, 434, each of which are fluidly connected to a corresponding signal reagent pack 420 through an aspiration line 450 and to the metering probe 400 through a metering line 446. The aspiration line 450 and the metering line 446 each comprise individual lines 448 and 445, respectively, extending to the pump head, shown in FIG. 3 as 422, a corresponding signal reagent pack 420 and the metering probe 400.

Referring to FIGS. 4(*a*)–4(*c*), each of the pumps of the prime/pump assembly 415 is a variable speed pump which includes the pump head 422 comprising a cylindrical ceramic liner 470 which houses a pump piston 474. The pump piston 474 reciprocally and rotationally moves synchronously within the ceramic liner 470 due to the connection of an eccentric cam 478 which is interconnected to the rotating shaft 482 of a pump motor (not shown). The motor is a stepper motor of conventional design that is capable of moving in fine steps. For purposes of this embodiment, the motor is capable of about 200 full steps (800 quarter steps per revolution).

In operation, each pump 430, 434 operates in four phases over the course of a revolution of the pump piston. Referring to FIG. 4(*a*), fluid is first aspirated including a suction (aspirate) phase from a signal reagent pack 420 through an individual aspiration line 448 via an inlet port 484 and into a pump chamber defined within the ceramic liner 470, the size of the chamber being defined by the linear position of the piston. During this portion of the metering cycle, the pump piston 474 is pulled back and a piston flat opens to the inlet port 484 of the pump permitting fluid to enter the defined chamber.

In a second phase, shown in FIG. 4(*b*), the piston 474 has rotated about 90 degrees within the ceramic liner 470 wherein both the inlet port 484 and an outlet port 486 of the pump are closed. The fluid is maintained within the pump chamber during this crossover phase.

Referring to FIG. 4(*c*), the pump piston 474 rotates an additional 90 degrees within the ceramic liner 470 and in addition the piston has also moved downwardly against the retained fluid in the pump chamber. The piston flat has opened to the outlet port 486 of the pump head permitting discharge of the fluid into the metering line 445 via the outlet port 486.

Finally and referring to FIG. 4(*d*), the pump piston 474 rotates to a position similar to that of FIG. 4(*b*) and both the inlet and outlet ports 484, 486 are closed. The piston repeats the above four cycles for each metering cycle and for each pump 430, 434, FIG. 3, wherein both pumps are utilized according to the present embodiment to aspirate and meter a quantity (about 50 μl) of signal reagent into a single reaction well through the pair of dispense tips 440, FIG. 3. Additional details relating to the overall features and operation of the pump are provided in U.S. Pat. No. 5,092,037, the entire contents of which are herein incorporated by reference.

Figure 5:
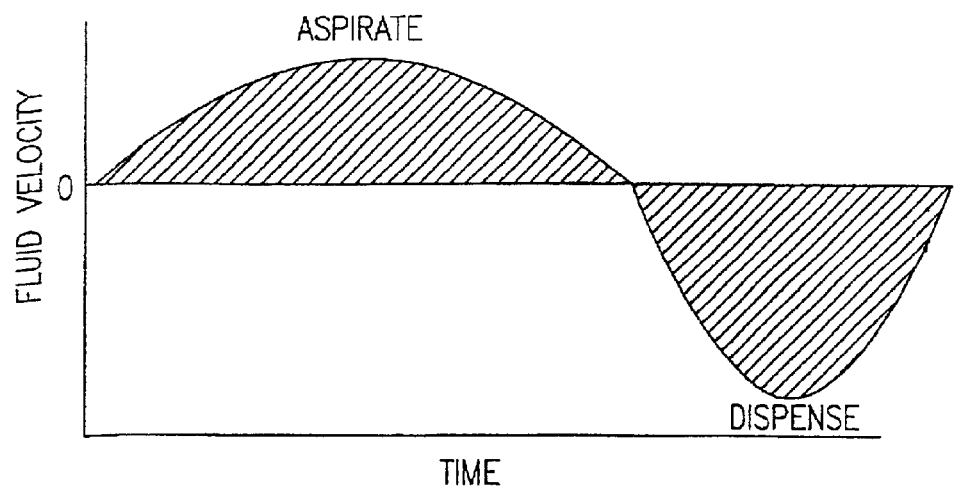
FIG. 5 is a baseline graphical representation of fluid flow rate profile for the signal reagent subsystem of FIGS. 1 and 3.

A representative fluid flow curve is illustrated in FIG. 5 for a metering cycle for the signal reagent subsystem using the above described prime/pump assembly 415. Typically, the speed of each pump motor is essentially constant in each phase of the metering cycle. For purposes of the present embodiment, the pump motor is maintained at about 1200 quarter steps per second in the aspirate phase and at about 2000 quarter steps per second in the dispense phase, each of the above phases requiring about 400 steps. It should be noted that for purposes of this discussion that this and succeeding profiles which are illustrated herein, the intermediate or crossover portions of the metering cycle are not illustrated. As a result of the eccentric cam and the angular position of the pump head, a variable flow rate is achieved by the fluid during each of the aspirate and dispense portions of the metering cycle. During this normal operation mode with the speed of each pump motor being essentially constant as noted above, the flow rate profile of the fluid is sinusoidal in nature varying between a maximum velocity and zero at the beginning and end of each of the aspirate and dispense phases.

An essential objective of the present invention is insuring that the dispense tips of the metering probe 400, FIG. 3, are essentially free of residual fluid at the end of the dispense phase of the metering cycle. As will be evident from the following embodiments, and by understanding the variations in dispense fluid flow, the fluid flow rate profile can be modified at any portion thereof in order to influence the fluid flow rate exiting the metering tip.

Figure 6:
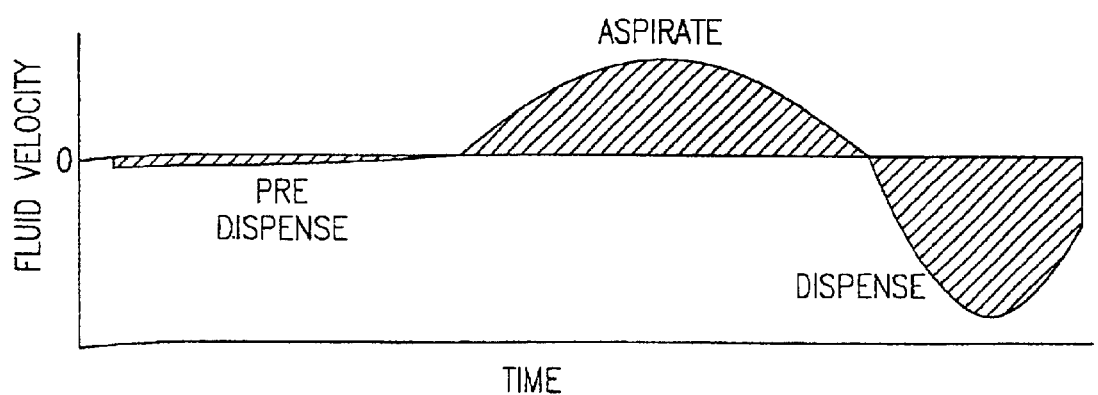
FIG. 6 is a graphical representation of a fluid flow rate profile in accordance with a first embodiment of the invention.

Referring to FIG. 6, a first embodiment involves the shifting of the "home" or stop position of the pump motor of the herein described signal reagent subsystem. This shift can be accomplished, for example, by utilizing a shift to a reference step location on the motor disc relative to an optical sensor (not shown). Shifting of this home position from a nominal or normal home position for a constant motor speed will cause a corresponding shift in the fluid flow profile of a phase of the metering cycle by effecting the position of the pump piston and cause the motor to cease pumping at an earlier point relative to the baseline fluid flow rate profile of FIG. 5. Therefore, the fluid velocity at the end of the dispense phase of the metering cycle is caused to be higher, the magnitude of this velocity increase depending of course upon the size of the shift from home position. For purposes of this embodiment, the home position is shifted within the crossover portion (not shown) between the aspirate and the dispense phases of the metering system cycle. According to the present embodiment, the home position is shifted by approximately 40 quarter steps within an 800 quarter step period representing a full rotation of the pump piston, causing an increase in fluid flow rate and a corresponding increase in the end fluid velocity of the dispense phase. The sufficiency of this increase in velocity results in a "dry" metering probe since the end velocity does not create perfusion of the fluid. The actual step offset applied should be determined based upon a combination of factors, including the nozzle geometry, the pump design, the resulting fluid flow rate profile, and fluid characteristics such as viscosity, surface tension, among others.

Still referring to FIG. 6 and depending upon the degree of shifting away from the home position, a quantity of fluid may be retained within the metering probe 400, FIG. 3, following the dispense phase of the metering cycle which must be dispensed prior to the aspirate phase. That is, shifting of the home position as described above can create a new "pre-dispense" phase for a metering cycle with regard to a subsequent reaction well 135, FIG. 2, this phase preceding the aspirate and dispense portions.

Though this particular dispense profile produces an essentially "dry" metering tip at the end of the dispense portion of the fluid flow profile, it was determined that the probe can subsequently become perfuse with fluid depending upon the amount of shifting of the home position and the amount of fluid to be dispensed during the now created pre-dispense phase. As evident from the profile of FIG. 6, the flow rate and therefore the velocity of fluid exiting the dispense tip during the pre-dispense is very low for a constant motor speed (about 200 quarter steps/second) and it has been determined empirically that very slight variations in the pump home position can cause significant fluid perfusion on the exterior of the dispense tip 440, FIG. 3, at the end of the pre-dispense portion. For example and in the present system, a 20 quarter step offset can cause 2.5 μl and a 10 quarter step offset can cause about 1.25 μl of residual fluid volume. The degree of influence in this regard is of course largely dependent upon the design of the metering probe and the speed of the motor, among others, this embodiment merely being exemplary. In general, however, pumps such as previously described having significant home position shifts will dispense larger amounts of fluid in the pre-dispense phase and subsequently smaller amounts of fluid in the final dispense phase using the natural speed of the pump motor.

Aside from the perfusion problem relating to any residual fluid, a further consideration that must be taken into account for the particular metering system is whether or not excessive splashing is produced in the reaction well by the dispensed fluid. In the presently described system and in order to minimize the amount of fluid on the end of the dispense tip of the metering probe at the end of the pre-dispense phase of the cycle while also reducing fluid splash, required an increase in the dispense volume to the 3–8 μl range (from a 0–2.5 μl range, according to the profile depicted in FIG. 6). That is, smaller fluid volumes tend to create splash when metered into the reaction well while larger volumes above this level (having dispense rates that reduce splashing) leave more fluid on the end of the tip of the metering probe at the end of the pre-dispense portion of the cycle.

Figure 7:
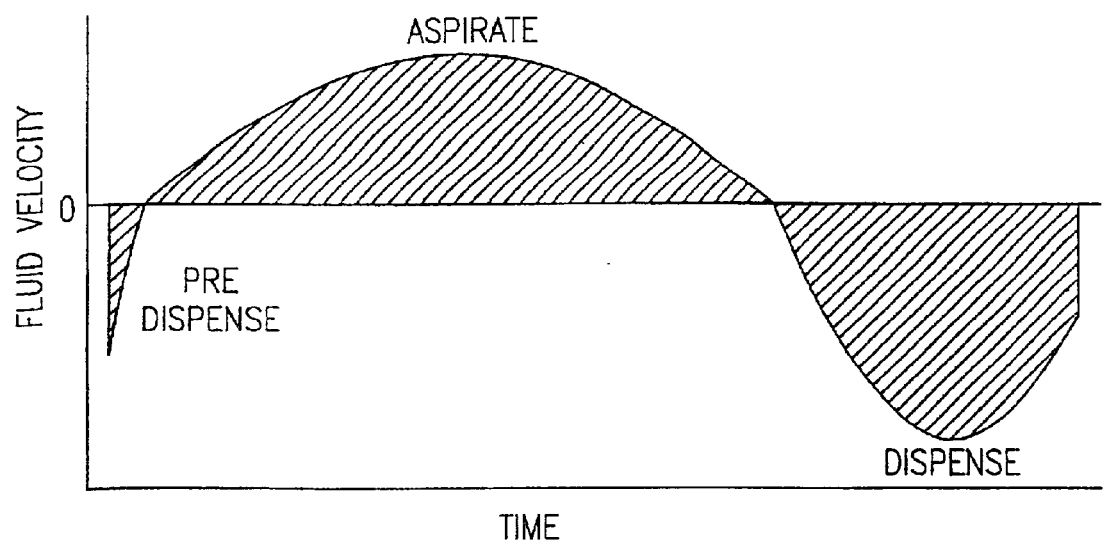
FIG. 7 is a graphical representation of a fluid flow rate profile in accordance with a second embodiment of the invention.

In an effort to alleviate the potential of perfusion in the pre-dispense phase of a metering event by reference to FIG. 7, and according to a second embodiment of the present invention, it was determined that an increase in dispensed fluid volume along with an increase in the pre-dispense fluid dispense rate, can be achieved by increasing the speed of the motor of the pump during that phase. In addition, it was determined that by increasing the speed of the pump motor to produce an increase in the pre-dispense rate of about 10 percent above the normal dispense rate reduces the amount of fluid on the end of the tip of the metering probe 400, FIG. 3, at the end of the pre-dispense phase of the metering system cycle without creating a substantial propensity for excessive splash in the reaction well 135, FIG. 2. According to this embodiment increasing the pump motor speed from about 200 quarter steps/second to about 2500 quarter steps/second, produced a sufficiently high fluid flow rate and hence velocity at the end of the dispense tip at the onset of pre-dispense to create a fluid shear effect sufficient to reduce or eliminate perfusion on the exterior thereof and without creating excessive splash in the reaction vessel.

It should be noted that the specific embodiment is exemplary for the signal reagent subsystem herein described. Other metering systems for use in clinical analyzers as well as a literally any metering system, regardless of application, utilizing a variable speed pump can benefit from the inventive concepts to either increase or decrease fluid flow rate/dispense velocity anywhere along the fluid flow rate profile through a similar modification thereof.

Figure 8:
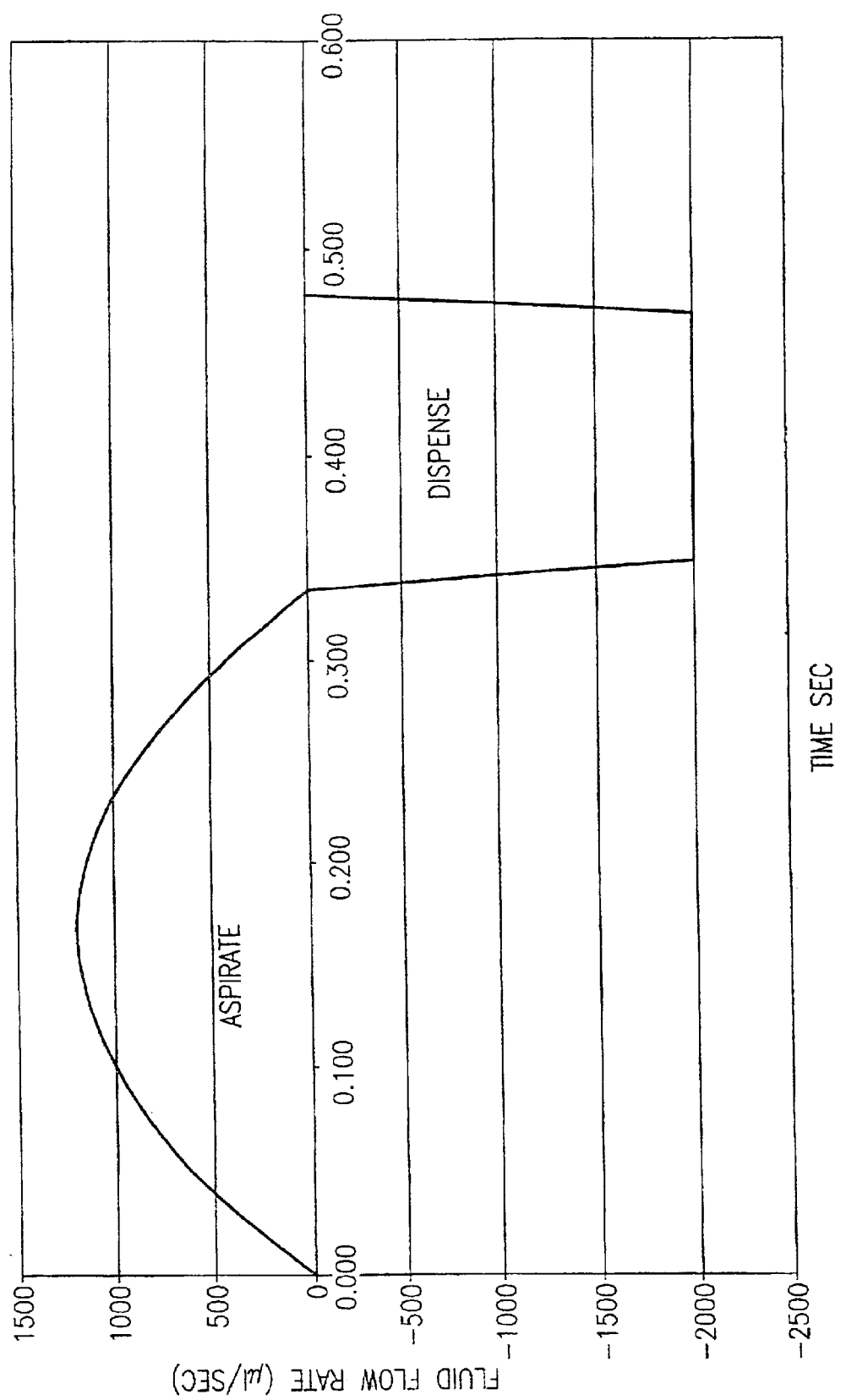
FIG. 8 is a graphical representation of a fluid flow rate profile in accordance with a third embodiment of the invention.
Figure 9:
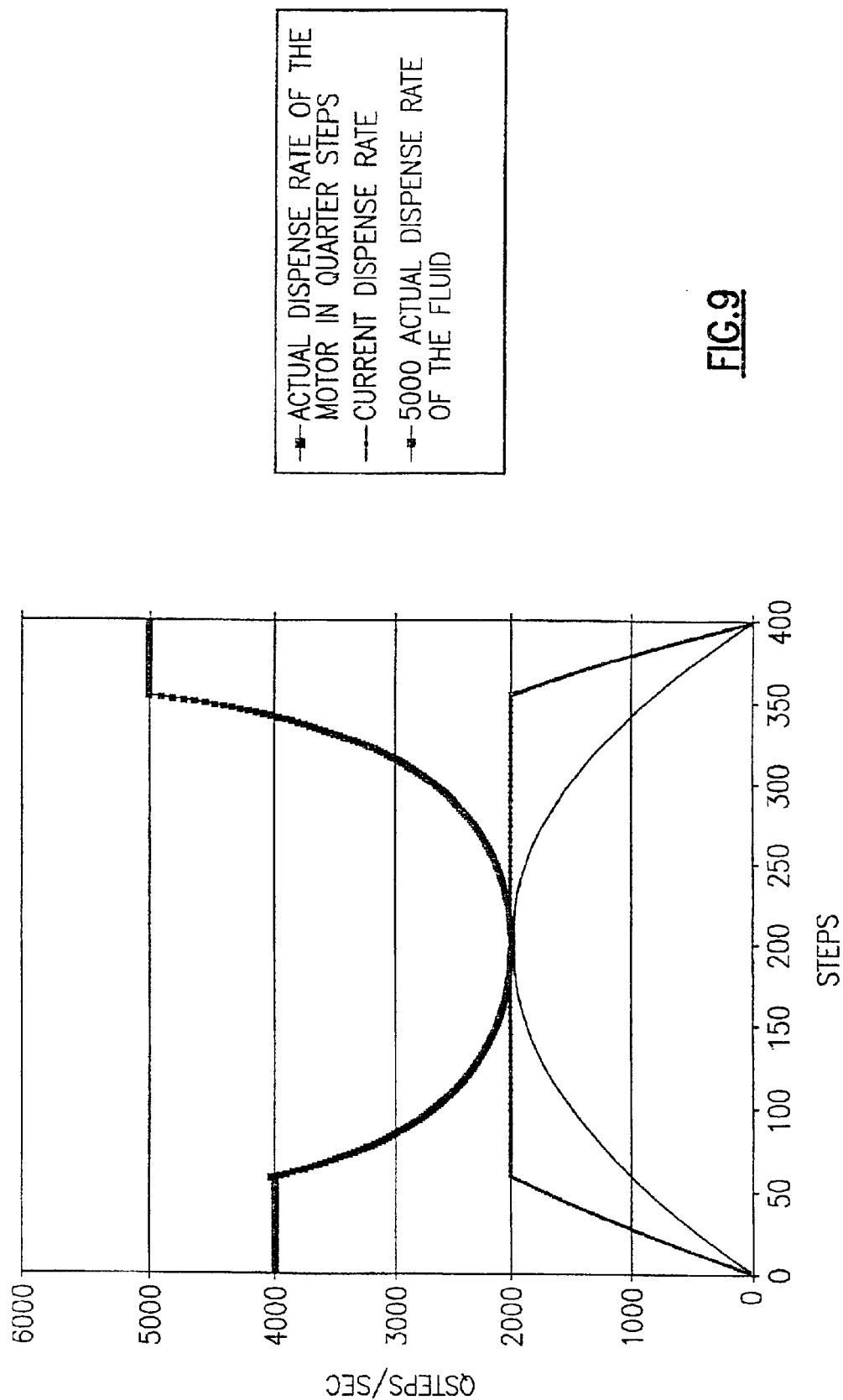
FIG. 9 is another graphical representation of the embodiment of FIG. 8.

Referring to FIGS. 8 and 9, the principles of the preceding embodiment can be more generally extended into the dispense phase of a normal metering system cycle, such as that previously shown in FIG. 5. According to a third embodiment, and by significant increasing pump motor speed at the end of the aspiration phase/beginning of the dispense phase and at the end of the dispense phase will cause the fluid flow rate exiting the dispense tip 440, FIG. 3, of the metering probe 400, FIG. 3, to remain mainly substantially constant throughout the dispense phase of the metering cycle. Ramping the motor speed becomes necessary due to the mechanical design of the variable speed pump wherein the eccentric cam 478, FIG. 4(*a*), of the pump causes fluid flow rate to be raised from zero at the onset of the dispense phase and gradually reduced to zero at the end of the dispense phase with the motor operating at a constant speed as previously noted with regard to FIG. 5.

It has been determined that ramping the speed of the pump motor at the beginning of the dispense phase and again at the end of the dispense phase relative to the normal constant motor speed (about 2000 quarter steps/second) produces a fluid flow rate profile which is essentially constant during the dispense phase of the metering cycle. Again certain factors will limit the increase in velocity at the dispense tip including the designs and geometry of the applicable metering nozzle and reaction vessel, the volumes of liquid being dispensed, and fluid viscosity, among others. According to this specific embodiment, the motor speed is increased from 1200 quarter steps/second to about 4000 quarter steps/second at the end of the aspiration phase in order to bring up the ramp profile more gradually. The motor speed is then is steadily decreased to normal speed (2000 quarter steps/second) during the maximum fluid flow rate portion of the dispense phase and is then ramped to a maximum of about 5000 quarter steps/second at approximately the end of the dispense phase. In essence and as best shown in FIG. 9, the shape of the herein applied motor speed profile is substantially an inverted version of the initial fluid flow rate profile.

According to the present embodiment, the home position of the pump motor is also shifted by approximately 0–30 steps in conjunction with the above noted ramping thereof. It was concluded that this combination effectively eliminated any perfusion of the exiting fluid relative to the dispense tip 440, FIG. 3, at the beginning of the dispense phase and also effectively caused the entirety of the predetermined fluid volume (e.g. 50 μl) to exit the tip during the dispense phase. Therefore, no pre-dispense phase was created.

As a more general proposition, it was determined that by varying the speed of the motor of the pump in the above manner by essentially inverting the variable fluid flow rate profile essentially produced a constant fluid flow rate profile during the majority of the dispense phase of the metering cycle. In essence and referring to FIG. 9, the velocity profile becomes essentially a square wave with a correspondingly increased fluid velocity at the end of the dispense tip which is maintained during the dispense phase.

Figure 10A:
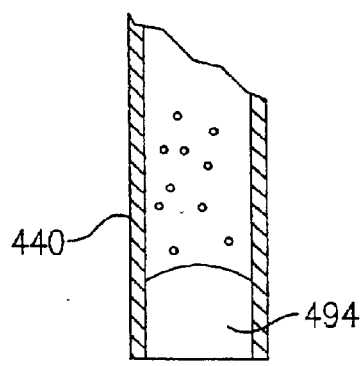
FIG. 10 is a partial sectioned end view of a dispense tip illustrating the effects of the increased fluid velocity of FIGS. 8 and 9 versus that of the baseline profile of FIG. 5.
Figure 10B:
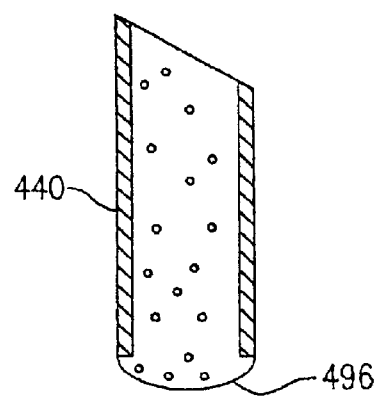

Creation of a square wave such as shown in the profile of FIG. 9 produces additional benefits. In addition to eliminating residual fluid at the end of the dispense cycle, the sudden and dramatic decrease in fluid flow also produces the formation of an air gap 494, FIG. 10, at the distal end of the dispense tip. This air gap 494 insulates the remaining fluid and creates a microenvironment having high relative humidity which assists in minimizing evaporation.

We claim:

1. A method for improving the dispensability of a metering system, said metering system including at least one dispense nozzle, a fluid supply, and at least one variable speed pump fluidly interconnecting said at least one dispense nozzle and said fluid supply, said at least one variable speed pump including a pump motor and having a mechanism which produces a variable fluid flow rate profile for a constant motor speed, said method including the steps of:

aspirating fluid from said fluid supply;

dispensing aspirated fluid through said at least one dispense nozzle; and effecting the relative velocity of the dispensed fluid by modifying a variable fluid rate flow using said pump motor during said dispensing step wherein said modifying step results in at least one of a change and a modification to said variable fluid flow rate profile and in which said relative velocity effecting step includes the step of offsetting a reference position of said pump motor in order to shift at least a portion of said variable fluid flow rate profile.

2. A method according to claim 1, wherein said variable speed pump produces a decrease in pump piston velocity at the end of said dispensing step, in which said offsetting step offsets said reference position to cause an increase in fluid dispense velocity at the end of said dispensing step.

3. A method according to claim 1, wherein said variable speed pump produces a sinusoidal fluid flow rate profile wherein the fluid flow rate becomes zero at the end of said dispensing step, wherein said offsetting step is applied to offset the end of said profile to provide a fluid flow rate at the end of said dispensing step.

4. A method according to claim 3, wherein a predetermined volume of fluid is dispensed onto a target, said method including the additional step of pre-dispensing residual fluid remaining from said dispensing step onto one of said target and a separate target prior to a subsequent aspirating and dispensing step.

5. A method according to claim 4, including the step of increasing the speed of said motor during at least said pre-dispensing step in order to increase the dispense velocity of said fluid.

6. A method for improving the dispensability of a metering system, said metering system including at least one dispense nozzle, a fluid supply, and at least one variable speed pump fluidly interconnecting said at least one dispense nozzle and said fluid supply, said at least one variable speed pump including a pump motor and having a mechanism which produces a variable fluid flow rate profile for a constant motor speed, said method including the steps of:
   aspirating fluid from said fluid supply;
   dispensing aspirated fluid through said at least one dispense nozzle; and
   effecting the relative velocity of the dispensed fluid modifying a variable fluid rate flow using said pump motor during said dispensing step wherein said modifying step results in at least one of a change and a modification to said variable fluid flow rate profile, wherein said relative velocity effecting step includes the step of applying a variation in motor speed according to a profile having a shape which is inverted relative to said variable fluid flow rate profile.

7. A method for improving the dispensability of a metering system, said metering system including at least one dispense nozzle, a fluid supply, and at least one variable speed pump fluidly interconnecting said at least one dispense nozzle and said fluid supply, said at least one variable speed pump including a pump motor and having a mechanism which produces a variable fluid flow rate profile for a constant motor speed, said method including the steps of:
   aspirating fluid from said fluid supply;
   dispensing aspirated fluid through said at least one dispense nozzle; and
   effecting the relative velocity of the dispensed fluid by modifying a variable fluid rate flow using said pump motor during said dispensing step wherein said modifying step results in at least one of a change and a modification to said variable fluid flow rate profile wherein said variable speed pump produces a sinusoidal fluid flow rate profile in which the beginning and end of said dispensing steps produce a fluid flow rate of zero from the dispense nozzle, said relative velocity effecting step including the step of increasing the speed of the pump motor along portions of said profile in order to increase the fluid flow rate.

8. A method for improving the dispensability of a metering system, said metering system including at least one dispense nozzle, a fluid supply, and at least one variable speed pump fluidly interconnecting said at least one dispense nozzle and said fluid supply, said at least one variable speed pump including a pump motor and having a mechanism which produces a variable fluid flow rate profile for a constant motor speed, said method including the steps of:
   aspirating fluid from said fluid supply;
   dispensing aspirated fluid through said at least one dispense nozzle; and
   effecting the relative velocity dispensed fluid by modifying a variable fluid rate flow using said pump motor during said dispensing step wherein said modifying step results in at least one of a change and a modification to said variable fluid flow rate profile wherein said variable speed pump produces a sinusoidal fluid flow rate profile, said relative velocity effecting step including the step of applying a variation in motor speed to said pump over said dispensing step which includes a shape which is essentially inverted relative to said fluid flow rate profile to produce a substantially constant dispense velocity during dispensing step.

9. A method for improving the dispensability of a metering system, said metering system including at least one dispense nozzle, a fluid supply, and at least one variable speed pump fluidly interconnecting said at least one dispense nozzle and said fluid supply, said at least one variable speed pump including a pump motor and having a mechanism which produces a variable fluid flow rate profile for a constant motor speed, said method including the steps of:
   aspirating fluid from said fluid supply;
   dispensing aspirated fluid through said at least one dispense nozzle; and
   effecting the relative velocity dispensed fluid by modifying a variable fluid rate flow using said pump motor during said dispensing step wherein said modifying step results in at least one of a change and a modification to said variable fluid flow rate profile, wherein said variable speed pump produces a fluid flow rate profile in which the fluid flow rate during the dispensing step is variable and characterized by an initially low fluid flow rate relative to the remaining portions of said profile, said relative velocity effecting step including the step of increasing the speed of said pump motor during at least the beginning of said dispensing step so as to increase the fluid flow rate sufficiently to prevent perfusion of dispensed fluid.

10. A method for improving the dispensability of a metering system used in a clinical analyzer, said metering system including at least one metering tip, a fluid supply, and at least one pump fluidly interconnecting said at least one metering tip and said fluid supply, said pump including a pump motor and having a mechanism which produces a variable fluid flow rate profile for a constant motor speed, said method including the steps of:
   a. aspirating fluid from said fluid supply using a metering tip attached to a proboscis;
   b. dispensing aspirated fluid through said metering tip into a reaction vessel; and
   c. effecting the relative velocity fluid dispensed by said metering system by modifying a variable fluid rate flow using said pump motor during said dispensing step wherein said modifying step results in at least one change and modification to said variable fluid flow rate profile, wherein said relative velocity effecting step includes the step of offsetting a reference position of said pump motor in order to shift at least a portion of said fluid flow rate profile.

11. A method according to claim 10, wherein said variable speed pump produces a decrease in pump piston velocity at the end of said dispensing step, in which said offsetting step offsets said reference position to cause an increase in fluid dispense velocity at the end of said dispensing step.

12. A method according to claim 10, wherein said variable speed pump produces a sinusoidal fluid flow rate profile wherein the fluid flow rate becomes zero at the end of said dispensing step, wherein said offsetting step is applied to offset the end of said profile to provide a non-zero fluid flow rate at the end of said dispensing step.

13. A method according to claim 12, wherein a predetermined volume of fluid is dispensed into a first reaction vessel, said method including the additional step of pre-dispensing residual fluid remaining from said dispensing step onto one of said first reaction vessel and a second reaction vessel prior to a subsequent aspirating and dispensing step therein.

14. A method according to claim 13, including the step of increasing the speed of said motor during at least said pre-dispensing step in order to increase the dispense velocity of said fluid.

15. A method for improving the dispensability of a metering system used in a clinical analyzer, said metering system including at least one metering tip, a fluid supply, and at least one pump fluidly interconnecting said at least one metering tip and said fluid supply, said pump including a pump motor and having a mechanism which produces a variable fluid flow rate profile for a constant motor speed, said method including the steps of:
  a. aspirating fluid from said fluid supply using a metering tip attached to a proboscis;
  b. dispensing aspirated fluid through said metering tip into a reaction vessel; and
  c. effecting the relative velocity fluid dispensed by said metering system by modifying a variable fluid rate flow using said pump motor during said dispensing step wherein said modifying step results in at one change and modification to said variable fluid flow rate profile, wherein said relative velocity effecting step includes the step of applying a variation in motor speed according to a profile having a shape which Is inverted relative to said fluid flow rate profile.

16. A method for improving the dispensability of a metering system used in a clinical analyzer, said metering system including at least one metering tip, a fluid supply, and at least one pump fluidly interconnecting said at least one metering tip and said fluid supply, said pump including a pump motor and having a mechanism which produces a variable fluid flow rate profile for a constant motor speed, said method including the steps of:
  a) aspirating fluid from said fluid supply using a metering tip attached to a proboscis;
  b) dispensing aspirated fluid through said metering tip into a reaction vessel; and
  c) effecting the relative velocity fluid dispensed by said metering system by modifying a variable fluid rate flow using said pump motor during said dispensing step wherein said modifying step results in at least one change and modification to said variable fluid flow rate profile, wherein said variable speed pump produces a sinusoidal fluid flow rate profile in which the beginning and end of said dispensing steps produces a fluid flow rate of zero from the metering tip, said relative velocity effecting step including the step of increasing the speed of the pump motor along portions of said profile in order to increase the fluid flow rate.

17. A method for improving the dispensability of a metering system used in a clinical analyzer, said metering system including at least one metering tip, a fluid supply, and at least one pump fluidly interconnecting said at least one metering tip and said fluid supply, said pump including a pump motor and having a mechanism which produces a variable fluid flow rate profile for a constant motor speed, said method including the steps of:
  a) aspirating fluid from said fluid supply using a metering tip attached to a proboscis;
  b) dispensing aspirated fluid through said metering tip into a reaction vessel; and
  c) effecting the relative velocity fluid dispensed by said metering system by modifying a variable fluid rate flow using said pump motor during said dispensing step wherein said modifying step results in at least one change and modification to said variable fluid flow rate profile, wherein said variable speed pump produces a sinusoidal fluid flow rate profile, said relative velocity effecting step including the step of applying a variation in motor speed to said pump over said dispensing step which includes a shape which is essentially inverted relative to said fluid flow rate profile to produce a substantially constant dispense velocity during dispensing step from said metering tip.

18. A method for improving the dispensability of a metering system used in a clinical analyzer, said metering system including at least one metering tip, a fluid supply, and at least one pump fluidly interconnecting said at least one metering tip and said fluid supply, said pump including a pump motor and having a mechanism which produces a variable fluid flow rate profile for a constant motor speed, said method including the steps of:
  a) aspirating fluid from said fluid supply using a metering tip attached to a proboscis;
  b) dispensing aspirated fluid through said metering tip into a reaction vessel; and
  c) effecting the relative velocity of fluid dispensed by said metering system by modifying a variable fluid rate flow using said pump motor during said dispensing step wherein said modifying step results in at least one change and modification to said variable fluid flow rate profile, wherein said variable speed pump produces a fluid flow rate profile in which the fluid flow rate during the dispensing step is variable and characterized by an initially low fluid flow rate relative to the remaining portions of said profile, said relative velocity effecting step including the step of increasing the speed of said pump motor during at least the beginning of said dispensing step so as to increase the fluid flow rate sufficiently to prevent perfusion of dispensed fluid relative to said metering tip.

19. A metering system comprising:
  a) at least one dispense nozzle;
  b) a fluid supply, and
  c) at least one variable speed pump fluidly interconnecting said at least one dispense nozzle and said fluid supply, said at least one variable speed pump including a motor and mechanical means for producing a variable fluid flow rate profile for a constant motor speed during at least one phase of a metering cycle including a dispensing phase, said system further including means for effecting the relative velocity of dispensed liquid through said at least one dispense nozzle using said pump motor by modifying a fluid flow rate using said motor during at least one phase of said metering cycle and resulting in at least one of a change and modification to the variable fluid flow rate profile A, wherein said relative velocity effecting means includes means for offsetting a reference position of said pump motor in order to shift at least a portion of said fluid flow rate profile.

20. A metering system according to claim 19, wherein said variable speed pump produces a decrease in pump piston velocity at the end of said dispensing step, wherein said reference position can be offset sufficiently to cause a relative increase in fluid dispense velocity at the end of a dispense phase.

21. A metering system according to claim 19, wherein said variable speed pump produces a sinusoidal fluid flow rate profile in which the fluid flow rate becomes zero at the end of a dispense phase, wherein said offsetting means is applied to offset the end of said profile to provide a non-zero fluid flow rate at the end of said dispense phase.

22. A metering system according to claim 21, wherein a predetermined volume of fluid is dispensed into a first target during the dispense phase and in which offsetting causes a residual volume of fluid remaining to complete the dispense phase of the cycle following a dispense phase requiring a pre-dispense phase in which the residual fluid volume is dispensed into one of the first and a separate second target prior to an aspiration phase.

23. A metering system according to claim 22, wherein said relative velocity effecting means includes means for increasing the speed of the pump motor during at least said pre-dispense phase in order to increase the dispense velocity of said fluid.

24. A metering system according to claim 19, wherein said system is used in a clinical analyzer.

25. A metering system comprising:
a) at least one dispense nozzle;
b) a fluid supply, and
c) at least one variable speed pump fluidly interconnecting said at least one dispense nozzle and said fluid supply, said at least one variable speed pump including a motor and mechanical means for producing a variable fluid flow rate profile for a constant motor speed during at least one phase of a metering cycle including a dispensing phase, said system further including means for effecting the relative velocity of dispensed liquid through said at least one dispense nozzle using said pump motor by modifying a fluid flow rate using said motor during at least one phase of said metering cycle and resulting in at least one of a change and modification to the variable fluid flow rate profile, wherein said relative velocity effecting means includes means for applying a variation in motor speed according to a profile having a shape which is substantially inverted relative to said fluid flow rate profile.

26. A metering system comprising:
a) at least one dispense nozzle;
b) a fluid supply, and
c) at least one variable speed pump fluidly interconnecting said at least one dispense nozzle and said fluid supply, said at least one variable speed pump including a motor and mechanical means for producing a variable fluid flow rate profile for a constant motor speed during at least one phase of a metering cycle including a dispensing phase, said system further including means for effecting the relative velocity of dispensed liquid through said at least one dispense nozzle using said pump motor by modifying a fluid flow rate using said motor during at least one phase of said metering cycle and resulting in at least one of a change and modification to the variable fluid flow rate profile, wherein said variable speed pump produces a sinusoidal fluid flow rate profile in which the beginning and end of said dispensing steps produces a fluid flow rate of zero from the metering tip, said relative velocity effecting means including means for increasing the speed of the pump motor along portions of said flow rate profile in order to increase the fluid flow rate.

27. A metering system comprising:
a) at least one dispense nozzle;
b) a fluid supply, and
c) at least one variable speed pump fluidly interconnecting said at least one dispense nozzle and said fluid supply, said at least one variable speed pump including a motor and mechanical means for producing a variable fluid flow rate profile for a constant motor speed during at least one phase of a metering cycle including a dispensing phase, said system further including means for effecting the relative velocity of dispensed liquid through said at least one dispense nozzle using said pump motor by modifying a fluid flow rate using said motor during at least one phase of said metering cycle and resulting in at least one of a change and modification to the variable fluid flow rate profile, wherein said variable speed pump produces a sinusoidal fluid flow rate profile, said relative velocity effecting means including means for applying a variation in motor speed to said pump during said dispense phase according to a motor speed profile having a shape which is essentially inverted relative to said fluid flow rate profile to produce a substantially constant dispense velocity during dispensing step.

28. A metering system comprising:
a) at least one dispense nozzle;
b) a fluid supply, and
c) at least one variable speed pump fluidly interconnecting said at least one dispense nozzle and said fluid supply, said at least one variable speed pump including a motor and mechanical means for producing a variable fluid flow rate profile for a constant motor speed during at least one phase of a metering cycle including a dispensing phase, said system further including means for effecting the relative velocity of dispensed liquid through said at least one dispense nozzle using said pump motor modifying a fluid flow rate using said motor during at least one phase of said metering cycle and resulting in at least one of a change and modification to the variable fluid flow rate profile, wherein said variable speed pump produces a fluid flow rate profile in which the fluid flow rate during the dispensing phase is variable and characterized by an initially low fluid flow rate relative to the remaining portions of said profile, said relative velocity effecting means including means for increasing the speed of said pump motor during at least the beginning of said dispensing step so as to increase the fluid flow rate sufficiently to prevent perfusion of dispensed fluid relative to said dispense nozzle.

29. A clinical analyzer comprising:

a housing;

a metering system disposed within said housing for aspirating and dispensing at least one fluid into at least one reaction vessel for purposes of obtaining a reaction; and a processing system for detecting at least one predetermined aspect of the reaction, said metering system including:

i) a proboscis retaining at least one of a plurality of metering tips;

ii) a fluid supply, and iii) at least one pump fluidly interconnecting said at least one proboscis and retained metering tip and said fluid supply, said pump including a motor and mechanical means for producing a variable fluid flow rate profile for a constant motor speed during at least one phase of a metering cycle including a dispensing phase, said analyzer further including means for effecting the relative velocity of fluid dispensed from said metering tip to modify a fluid flow rate of said pump during at least one phase of said metering cycle and thereby at least one of changing and modifying the variable fluid flow rate profile, wherein said relative velocity effecting means includes means for offsetting a reference position of said pump motor in order to shift at least a portion of said fluid flow rate profile.

30. A clinical analyzer according to claim 29, wherein said variable speed pump produces a decrease in pump piston velocity at the end of said dispensing step, wherein said reference position can be offset sufficiently to cause a relative increase in fluid dispense velocity at the end of a dispense phase.

31. A clinical analyzer according to claim 29, wherein said variable speed pump produces a sinusoidal fluid flow rate profile in which the fluid flow rate becomes zero at the end of a dispense phase, wherein said offsetting means is applied to offset the end of said profile to provide a non-zero fluid flow rate at the end of said dispense phase.

32. A clinical analyzer according to claim 31, wherein a predetermined volume of fluid is dispensed from said metering tip into a first reaction vessel during the dispense phase and in which offsetting causes a residual volume of fluid remaining to complete the dispense phase of the cycle following a dispense phase requiring a pre-dispense phase in which the residual fluid volume is dispensed into one of the first and a separate second reaction vessel housed in said analyzer prior to an aspiration phase.

33. A clinical analyzer according to claim 32, wherein said relative velocity effecting means includes means for increasing the speed of the pump motor during at least said pre-dispense phase in order to increase the dispense velocity of said fluid.

34. A clinical analyzer comprising:

a housing;

a metering system disposed within said housing for aspirating and dispensing at least one fluid into at least one reaction vessel for purposes of obtaining a reaction; and a processing system for detecting at least one predetermined aspect of the reaction, said metering system including:

i) a proboscis retaining at least one of a plurality of metering tips;

ii) a fluid supply, and iii) at least one pump fluidly interconnecting said at least one proboscis and retained metering tip and said fluid supply, said pump including a motor and mechanical means for producing a variable fluid flow rate profile for a constant motor speed during at least one phase of a metering cycle including a dispensing phase, said analyzer further including means for effecting the relative velocity of fluid dispensed from said metering tip to modify a fluid flow rate of said pump during at least one phase of said metering cycle and thereby at least one of changing and modifying the variable fluid flow rate profile, wherein said relative velocity effecting means includes means for applying a variation in motor speed according to a profile having a shape which is substantially inverted relative to said fluid flow rate profile.

35. A clinical analyzer comprising:

a housing;

a metering system disposed within said housing for aspirating and dispensing at least one fluid into at least one reaction vessel for purposes of obtaining a reaction; and a processing system for detecting at least one predetermined aspect of the reaction, said metering system including:

i) a proboscis retaining at least one of a plurality of metering tips;

ii) a fluid supply, and iii) at least one pump fluidly interconnecting said at least one proboscis and retained metering tip and said fluid supply, said pump including a motor and mechanical means for producing a variable fluid flow rate profile for a constant motor speed during at least one phase of a metering cycle including a dispensing phase, said analyzer further including means for effecting the relative velocity of fluid dispensed from said metering tip to modify a fluid flow rate of said pump during at least one phase of said metering cycle and thereby at least one of changing and modifying the variable fluid flow rate profile, wherein said variable speed pump produces a sinusoidal fluid flow rate profile in which the beginning and end of said dispensing steps produces a fluid flow rate of zero from the metering tip, said relative velocity effecting means including means for increasing the speed of the pump motor along portions of said flow rate profile in order to increase the fluid flow rate.

36. A clinical analyzer comprising:

a housing;

a metering system disposed within said housing for aspirating and dispensing at least one fluid into at least one reaction vessel for purposes of obtaining a reaction; and a processing system for detecting at least one predetermined aspect of the reaction, said metering system including:

i) a proboscis retaining at feast one of a plurality of metering tips;

ii) a fluid supply, and iii) at least one pump fluidly interconnecting said at least one proboscis and retained metering tip and said fluid supply, said pump including a motor and mechanical means for producing a variable fluid flow rate profile for a constant motor speed during at least one phase of a metering cycle including a dispensing phase, said analyzer further including means for effecting the relative velocity of fluid dispensed from said metering tip to modify a fluid flow rate of said pump during at least one phase of said metering cycle and thereby at least one of changing and modifying the variable fluid flow rate profile, wherein said variable speed pump produces a sinusoidal fluid flow rate profile, said relative velocity effecting means including means for applying a variation in motor speed to said pump during said dispense phase according to a motor speed profile having a shape which is essentially inverted relative to said fluid flow rate profile to produce a substantially constant dispense velocity during dispensing step.

37. A clinical analyzer comprising:

a housing;

a metering system disposed within said housing for aspirating and dispensing at least one fluid into at least one reaction vessel for purposes of obtaining a reaction; and a processing system for detecting at least one predetermined aspect of the reaction, said metering system including:

i) a proboscis retaining at least one of a plurality of metering tips;

ii) a fluid supply, and iii) at least one pump fluidly interconnecting said at least one proboscis and retained metering tip and said fluid supply, said pump including a motor and mechanical means for producing a variable fluid flow rate profile for a constant motor speed during at least one phase of a metering cycle including a dispensing phase, said analyzer further including means for effecting the relative velocity of fluid dispensed from said metering tip to modify a fluid flow rate of said pump during at least one phase of said metering cycle and thereby at least one of changing and modifying the variable fluid flow rate profile, wherein said variable speed pump produces a fluid flow rate profile in which the fluid flow rate during the dispensing phase is variable and characterized by an initially low fluid flow rate relative to the remaining portions of said profile, said relative velocity effecting means including means for increasing the speed of said pump motor during at least the beginning of said dispensing step so as to increase the fluid flow rate sufficiently to prevent perfusion of dispensed fluid relative to said dispense nozzle.

* * * * *